United States Patent
Dunlop

(10) Patent No.: US 7,588,560 B1
(45) Date of Patent: Sep. 15, 2009

(54) FEMALE CATHETER

(76) Inventor: Seoras Tomas Dunlop, 85 Manistee St., Pawtucket, RI (US) 02861

( * ) Notice: Subject to any disclaimer, the term of this patent is extended or adjusted under 35 U.S.C. 154(b) by 0 days.

(21) Appl. No.: 11/800,839

(22) Filed: May 8, 2007

(51) Int. Cl.
*A61F 5/44* (2006.01)

(52) U.S. Cl. ............... 604/329; 604/347; 604/355; 4/144.3

(58) Field of Classification Search .......... 604/329, 604/347, 355
See application file for complete search history.

(56) References Cited

U.S. PATENT DOCUMENTS

| | | | |
|---|---|---|---|
| 4,198,979 A * | 4/1980 | Cooney et al. | 604/329 |
| 4,233,978 A | 11/1980 | Hickey | |
| 4,270,539 A * | 6/1981 | Frosch et al. | 604/347 |
| 4,484,917 A | 11/1984 | Blackmon | |
| 4,563,183 A | 1/1986 | Barrodale et al. | |
| 4,690,677 A * | 9/1987 | Erb | 604/329 |
| 4,886,508 A | 12/1989 | Washington | |
| 5,593,389 A * | 1/1997 | Chang | 604/174 |
| D418,918 S | 1/2000 | Cunningham | |
| 6,428,521 B1 | 8/2002 | Droll | |
| 2001/0037098 A1* | 11/2001 | Snyder | 604/331 |

* cited by examiner

*Primary Examiner*—Tatyana Zalukaeva
*Assistant Examiner*—Ilya Y Treyger
(74) *Attorney, Agent, or Firm*—Salter & Michaelson

(57) ABSTRACT

A catheter includes a urinary tube having proximal and distal ends intercoupling a passage for receiving the discharge of urine from the urethera with the urinary tube distal end for coupling to a collection means. A resilient and deformable flared flange member is formed integral with the proximal end of the urinary tube, has a centered port contiguous with the urinary tube passage, has a peripheral edge that at least in part defines an annular proximal facing contact surface and an opposed annular distal facing contact surface. The peripheral edge covers an area that is greater than the cross-sectional area of the urinary tube. An adhesive component is disposed on the annular proximal facing contact surface.

5 Claims, 7 Drawing Sheets

FEMALE CATHETER

TECHNICAL FIELD

The present invention relates in general to a female catheter. More particularly, the present invention pertains to a female catheter that is of simplified construction and that can be easily applied.

BACKGROUND OF THE INVENTION

The containment and/or collection of urine from an incontinent female is a problem for millions of women. In providing a urine collection device for females, reliable functioning, no matter whether the flow is small or large, or the onset is sudden, is of utmost importance. Few things can be more embarrassing than a sudden uncontrolled urination, particularly when it is noticed by other people. It is highly desirable that any ladies incontinence device be able to handle this possibility without leakage. The nature of the condition mandates that many wearers of an incontinence device keep the device in place against their person for relatively long periods of time. As a result, comfort is quite important as is freedom from irritation and chafing which may result from normal movement of the wearer with the device in place. It is also highly desirable to remove the waste fluid from any contact with the body as soon as possible to minimize irritation and infection.

Many of the prior art devices are highly intrusive and prone to causing infection. Refer to devices found in U.S. Pat. Nos. 4,233,978; 4,484,917; 4,563,183 and 4,886,508. These devices are typically quite large and too easily cause cross-contamination and related infections. Furthermore, although some of these devices do show the use of an adhesive, such as shown in the '183 patent, the device covers too large an area and substantially increases the likelihood of infection and cross-contamination.

Accordingly, it is an object of the present invention to provide an improved female catheter device that is relatively compact and unobtrusive.

A further object of the present invention is to provide a female catheter that is constructed and arranged so as to eliminate infections, such as bladder infections, that have been common with prior art devices.

Another object of the present invention is to provide a female catheter that is readily applied, is effective in gathering all dispensed fluids and is also readily removable and replaceable.

Still another object of the present invention is to provide an improved female catheter that is relatively small in size and that can be readily applied even by an unskilled person.

SUMMARY OF THE INVENTION

In accordance with the present invention there is provided a female external catheter comprising: a urinary tube having proximal and distal ends intercoupling a passage for receiving therethrough the discharge of urine from the urethera with the urinary tube distal end for coupling to a collection means; a resilient and deformable flared flange member that is formed integral with the proximal end of the urinary tube, that has a centered port contiguous with the urinary tube passage, that has a peripheral edge that at least in part defines an annular proximal facing contact surface and an opposed annular distal facing contact surface, and that the peripheral edge covers an area that is greater than the cross-sectional area of the urinary tube; and an adhesive component disposed on the annular proximal facing contact surface. The resilient and deformable flared flange member is applied by manual contact with the annular distal facing contact surface so as to adhere the annular proximal facing contact surface at the fossa navicularis by means of the adhesive component. The resilient and deformable flared flange member peripheral edge is constructed and arranged so as to be within the bounds defined by the labium minus when applied. The resilient and deformable flared flange member in its applied position establishes an alignment between the port and the uretheral meatusk.

In accord with other aspects of the present invention the urinary tube may have a length on the order of 3-6 inches. The resilient and deformable flange member may have a somewhat funneled shape; the resilient and deformable flange member may be formed in a calla lily configuration; the resilient and deformable flange member is preferable oval shaped at its peripheral edge; the mean diameter of the peripheral edge may be in a range between 15 and 30 millimeters; the thickness of the resilient and deformable flange member may be on the order of 1-2 millimeter; a peel-off tab may cover the adhesive component and be removable to expose an adhesive layer; the wall thickness of the urinary tube is preferably greater than the thickness of the resilient and deformable flange member; the urinary tube wall thickness may be on the order of 1-2 millimeters; the thickness of the resilient and deformable flange member may be on the order of one millimeter; the proximal facing contact surface is preferably an annular surface that surrounds the uretheral meatus when applied; the area covered by the annular surface is may be in a range on the order of 150-300 square millimeters.

In accord with another version of the invention there is provided a method of applying a female catheter at the uretheral meatus of the female anatomy for the purpose of enabling a discharge of urine through a urinary tube having proximal and distal ends intercoupling a passage for receiving therethrough the discharge of urine from the urethera; said urinary tube distal end for coupling to a collection means; providing a resilient and deformable flared flange member that is formed integral with the proximal end of the urinary tube, that has a centered port contiguous with the urinary tube passage, that has a peripheral edge that at least in part defines an annular proximal facing contact surface and an opposed annular distal facing contact surface; providing an adhesive component disposed on the annular proximal facing contact surface; applying the resilient and deformable flared flange member by manual contact of the user with the annular distal facing contact surface so as to adhere the annular proximal facing contact surface at the fossa navicularis by means of the adhesive component; the applying step including arranging the resilient and deformable flared flange member peripheral edge so as to be within the bounds defined by the labium minus when applied; the applying step further aligning the resilient and deformable flared flange member port with the uretheral meatus.

BRIEF DESCRIPTION OF THE DRAWINGS

The foregoing and other objects, advantages and features of the present invention will become apparent upon a reading of the following detailed description when taken in conjunction with the accompanying drawings, wherein.

DETAILED DESCRIPTION

Reference is now made to a preferred embodiment of the present invention shown in FIGS. 1-11. The female external catheter may be considered as basically comprises of two main components that are integrally formed into a single piece catheter that is readily applied about the uretheral meatus. Several of the drawings shown herein depict the female anatomy and the manner in which the placement of the catheter of the present invention is made so that optimum conditions are attained. This is possible by the placement of the flange member of the catheter between the bounds defined by the labium minus when applied. Thus, the flange member itself has to have sufficient size to enable a secure fixing of the position of the catheter, and yet has to be of a size that fits within the bounds of the labium minus.

Figure 4:
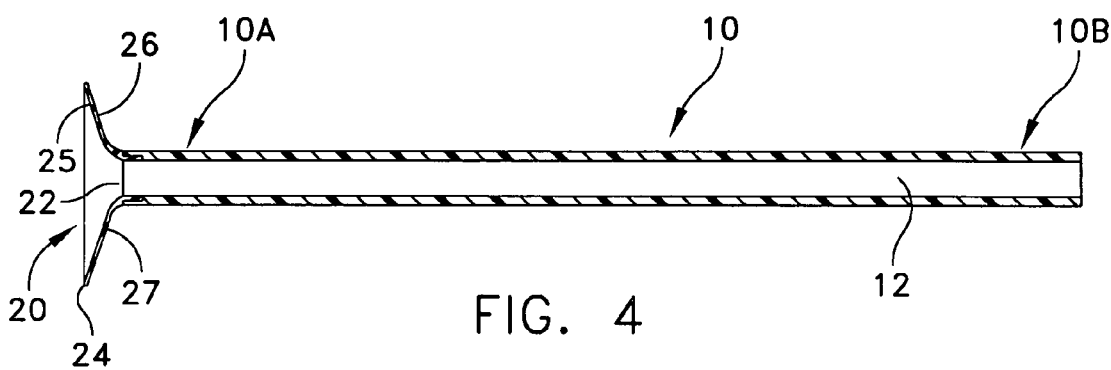
FIG. 4 is a cross-sectional view taken along line 4-4 of FIG. 3.
Figure 5:
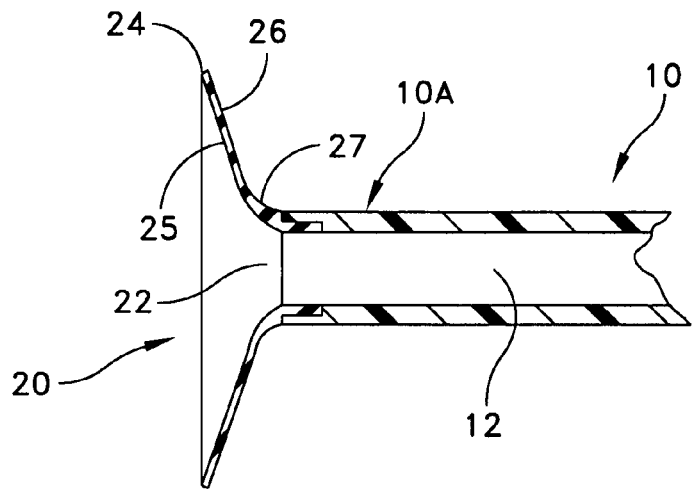
FIG. 5 is a an enlarged cross-sectional view like of a part of the female catheter shown in FIG. 4.
Figure 6:
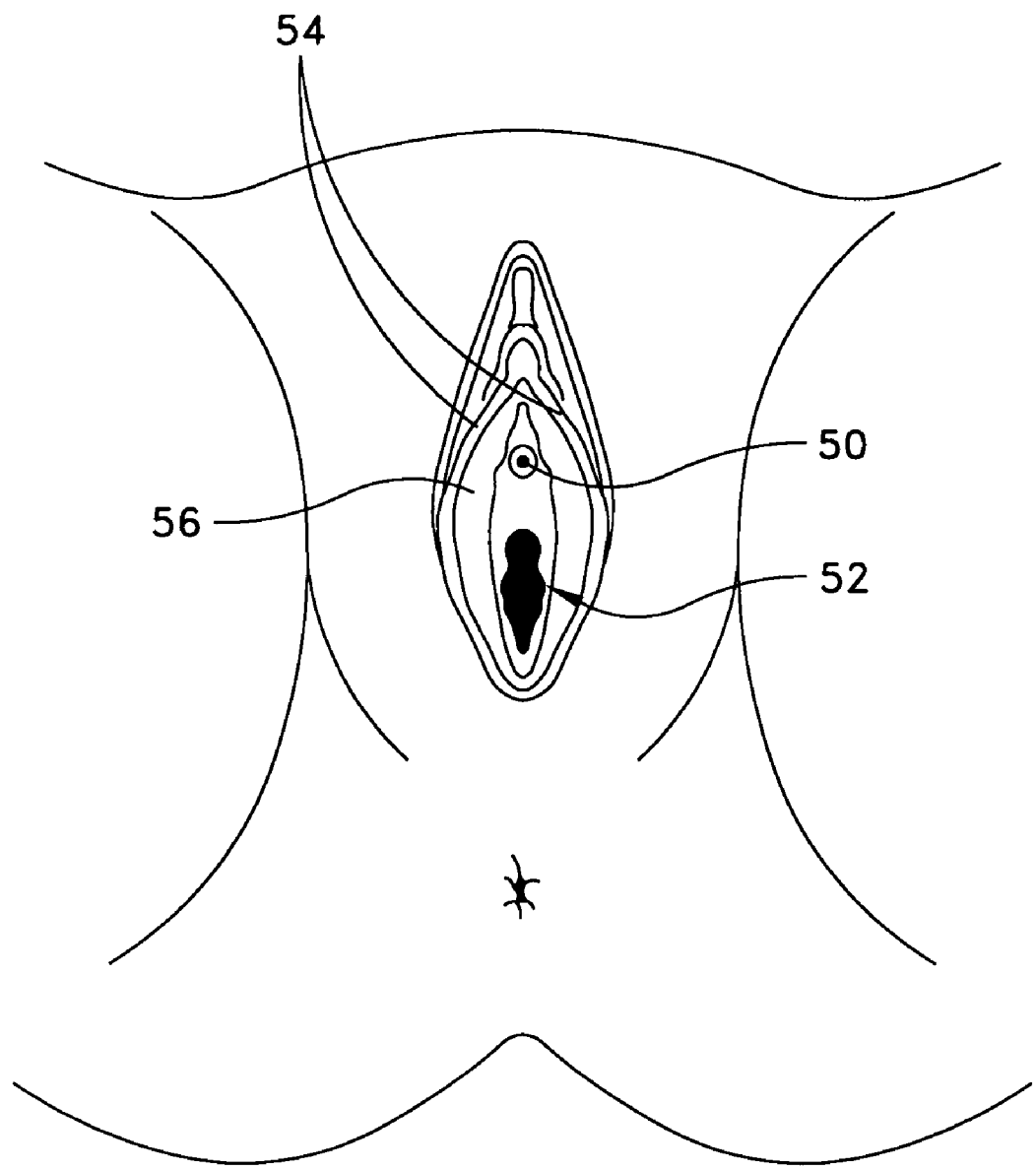
FIG. 6 is an illustration of the female anatomy where the catheter is to be applied.
Figure 11:
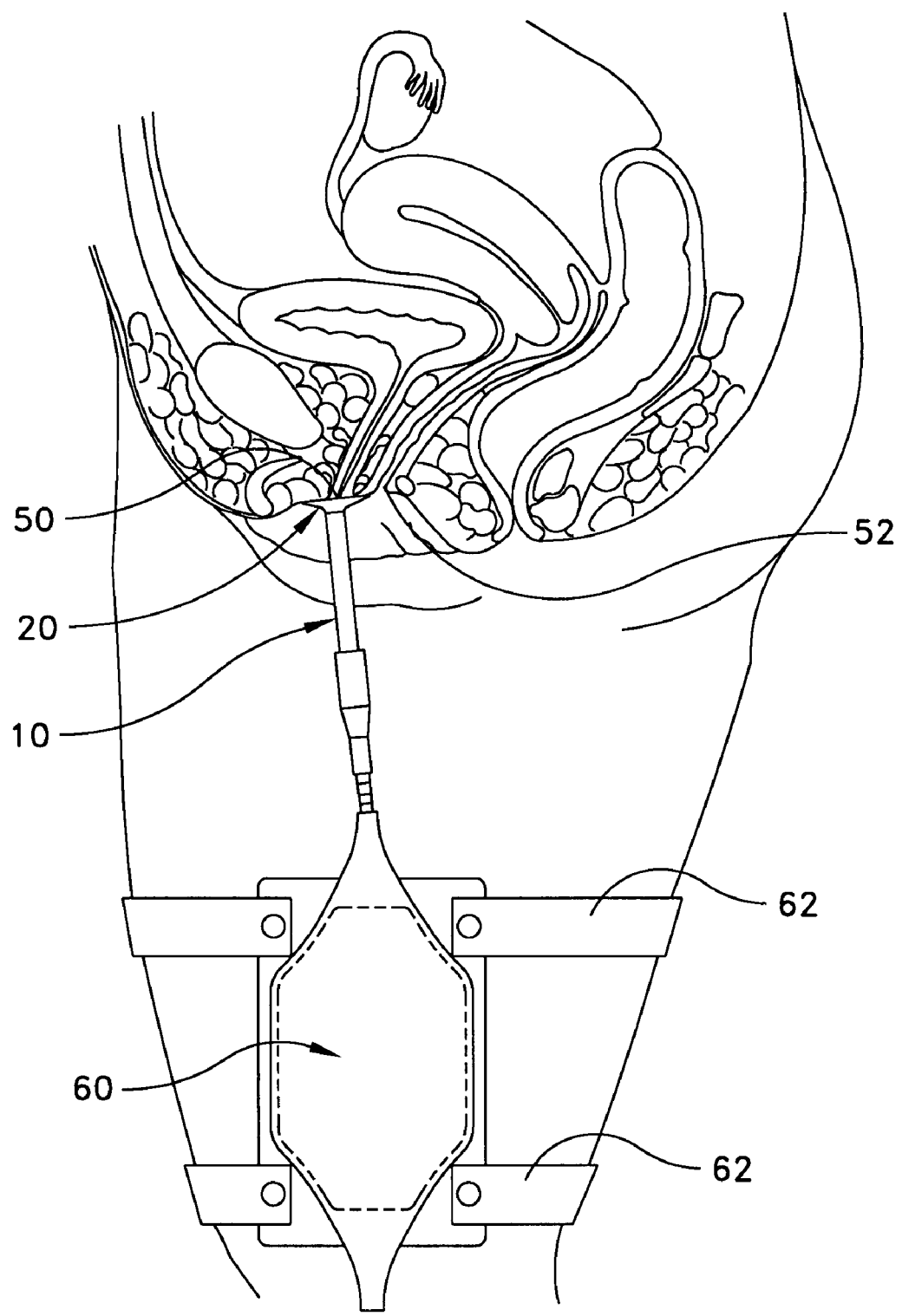
FIG. 11 illustrates the use of the female catheter with a collection bag.

The female catheter of the present invention thus includes a urinary tube 10 having a proximal end 10A and a distal end 10B. The urinary tube 10 is hollow, thus having a passage 12 for receiving therethrough the discharge of urine from the urethera. The urinary tube 10 distal end 10B is for coupling to a collection means, as illustrated in FIG. 11 and to be described in further detail hereinafter. The female catheter also includes a resilient and deformable flared flange member 20 that is formed integral with the proximal end 10A of the urinary tube 10. The resilient and deformable flared flange member 20 has a centered port 22 contiguous with the urinary tube passage 12 as shown in FIGS. 4 and 5. The resilient and deformable flared flange member 20 has a peripheral edge 24 that at least in part defines an annular proximal facing contact surface 25 and an opposed annular distal facing contact surface 26. The peripheral edge 24 covers an area that is greater than the cross-sectional area of the urinary tube 10. Herein reference to "proximal" means closer to the anatomy and "distal" means away from the anatomy.

An adhesive component 30 is disposed on the annular proximal facing contact surface 25. The adhesive is a medically approved adhesive that may be sprayed onto the annular proximal facing contact surface 25, or may be applied in any other manner. A pull-tab 40 is used to cover the adhesive layer and is readily pulled from the contact face surface 25 so as to expose the adhesive layer 30.

Figure 1:
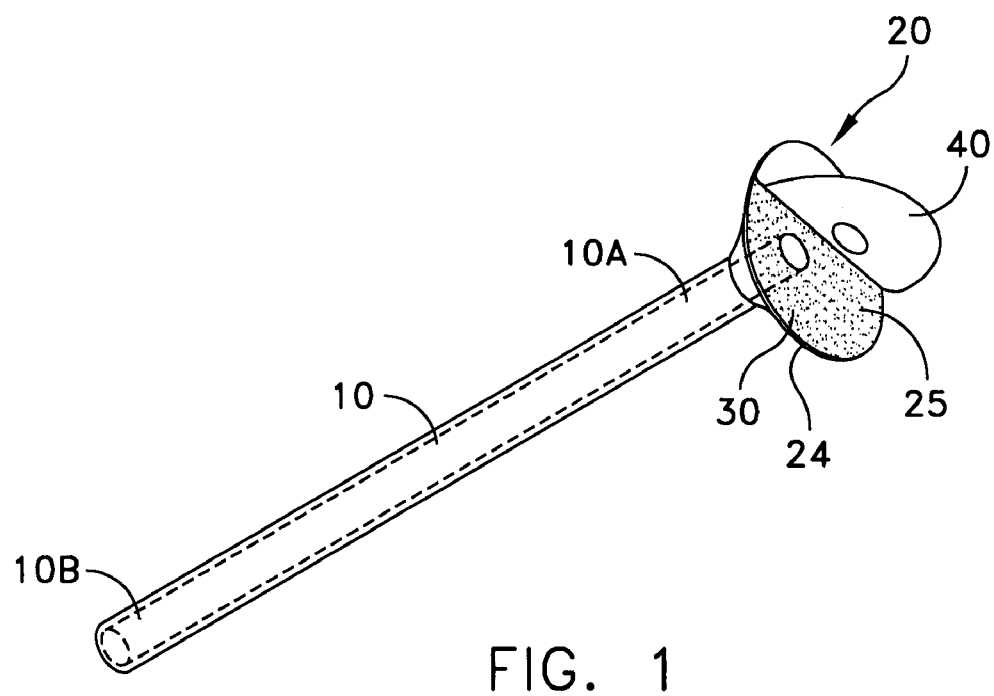
FIG. 1 is a perspective view of a preferred embodiment of the female catheter of the present invention with a stick-on label being peeled off.
Figure 2:
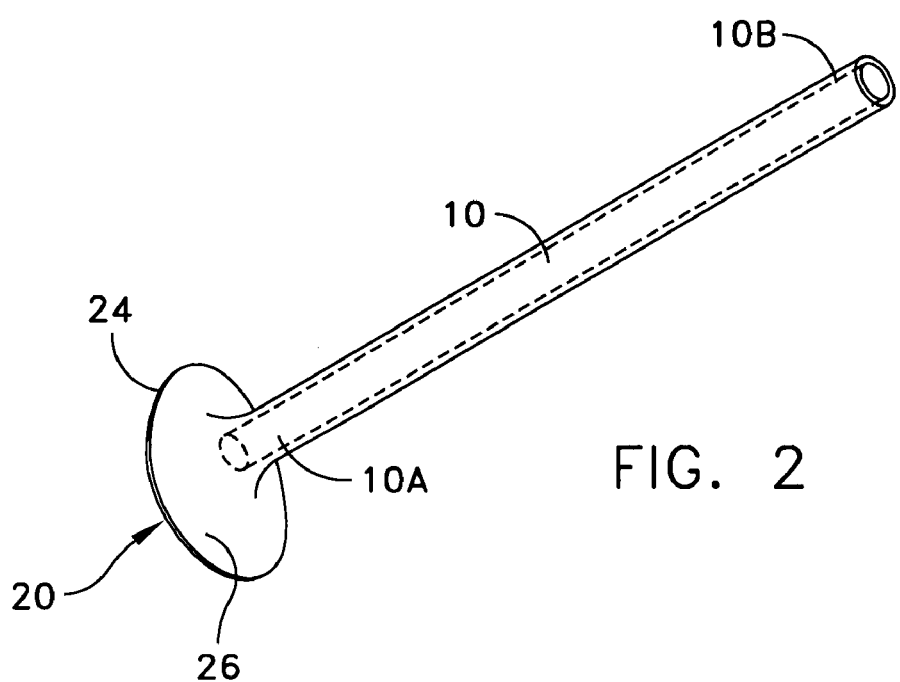
FIG. 2 is a reversed perspective view of the female catheter of FIG. 1.
Figure 3:
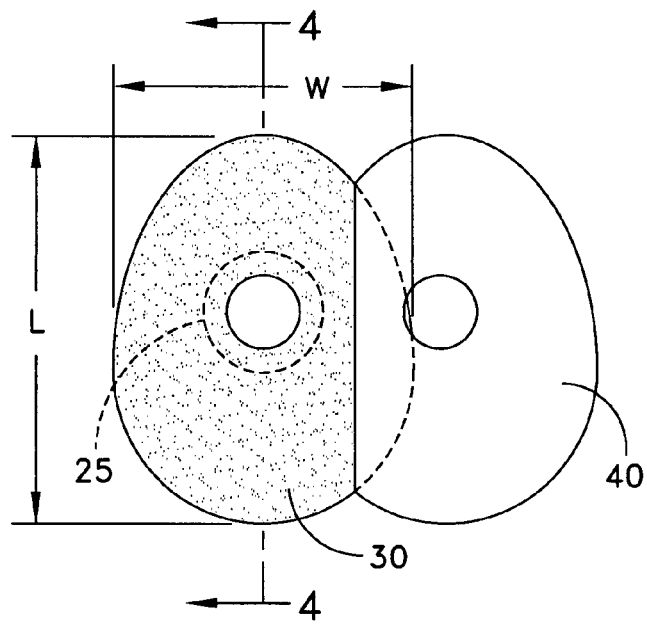
FIG. 3 an end view of the female catheter of FIGS. 1 and 2.

The resilient and deformable flared flange member 20 is constructed of a resilient and pliable plastic material such as of latex or silicone. It is preferably in the shape of a flared, funnel-shaped or calla lily configuration. The shape of a preferred flange member is shown in FIG. 3. This is an oval shape in that direction, somewhat elliptical and having a width W that is less that its length L. FIG. 3 also shows that the entire surface 25 is covered with the adhesive layer. In another embodiment only the area 25A may be covered as that is the only area where contact is made with the anatomy when the catheter is applied. Area 25A is annular. The area of the area 25A is on the order of 150-300 square millimeters.

Figure 7:
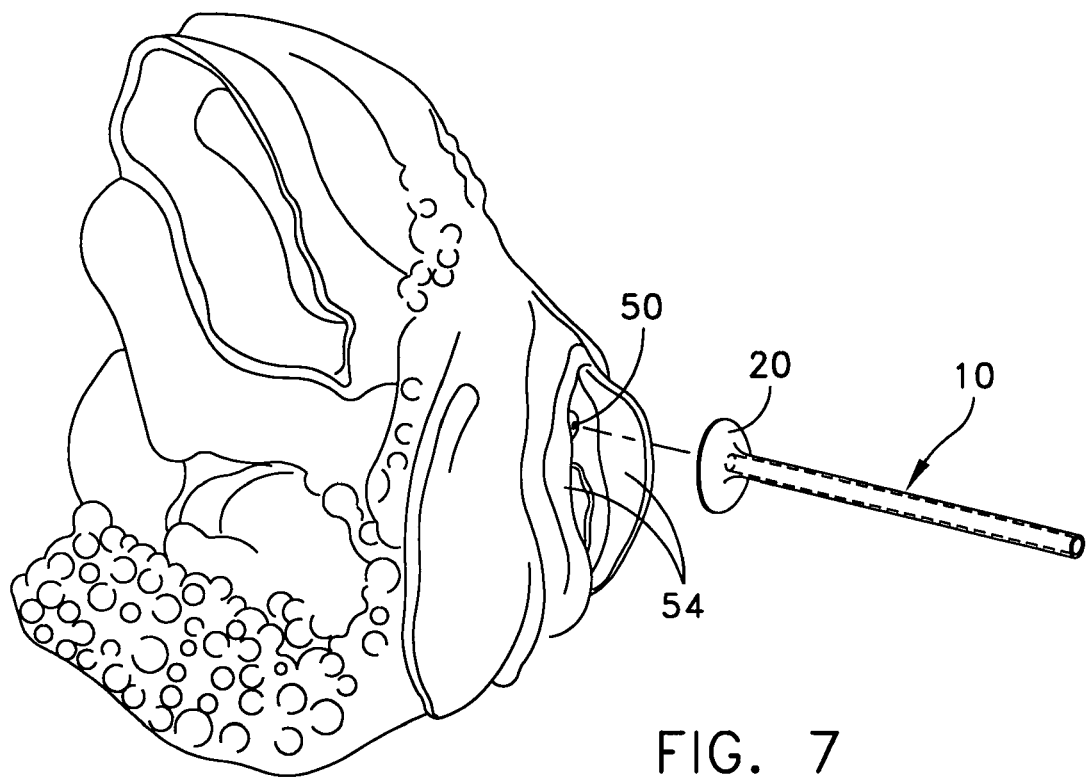
FIG. 7 is a perspective view illustrating the female catheter of the present invention in relationship to the female anatomy.
Figure 8:
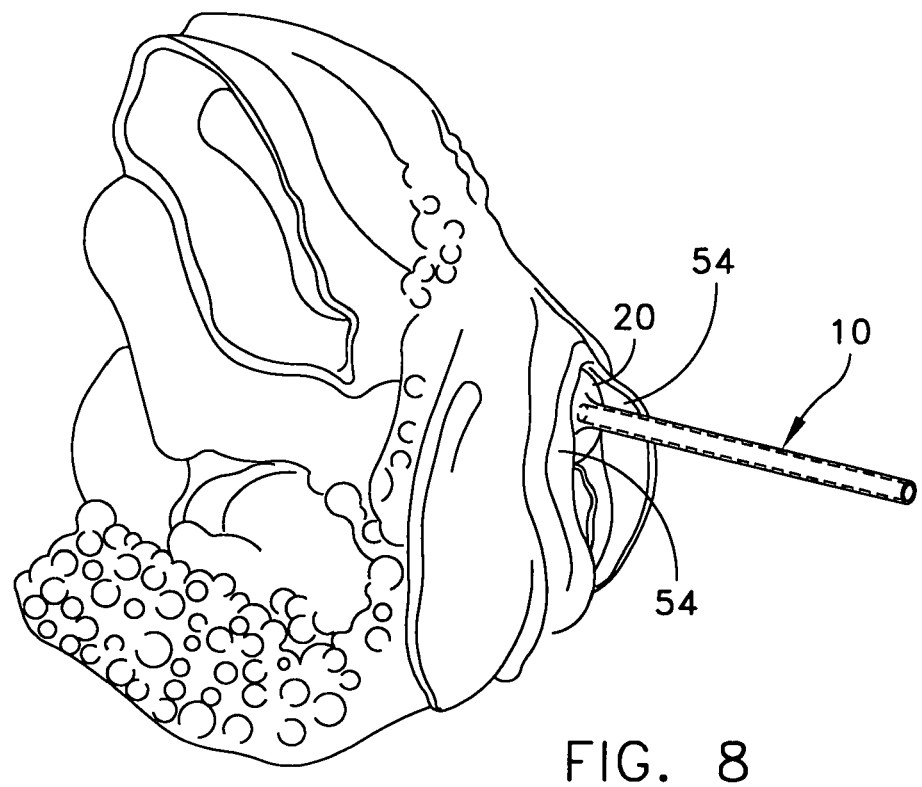
FIG. 8 is a perspective view illustrating the female catheter of the present invention as applied to the female anatomy.
Figure 9:
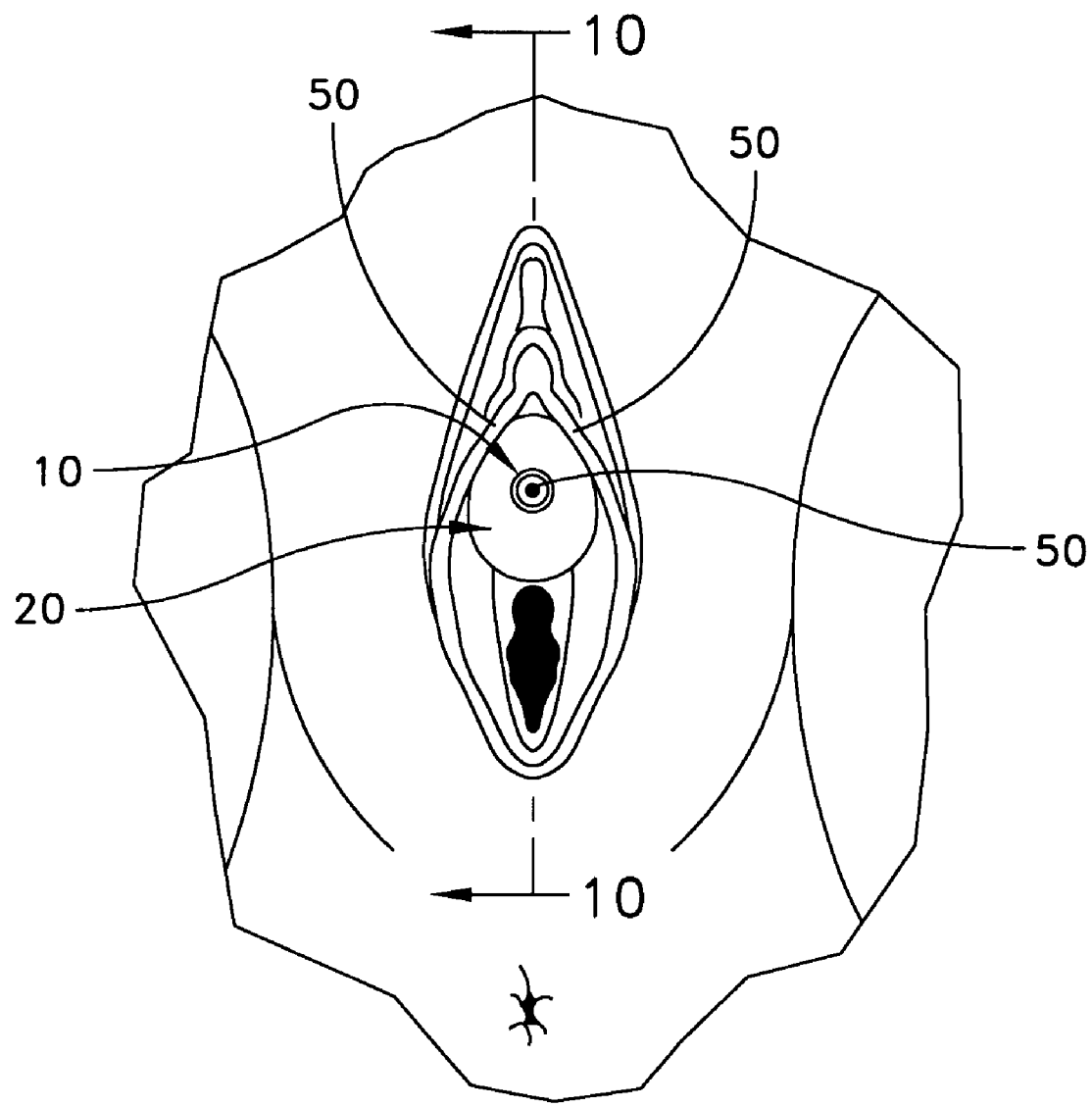
FIG. 9 shows a frontal view with the female catheter of the present invention as applied at the urethrae.
Figure 10:
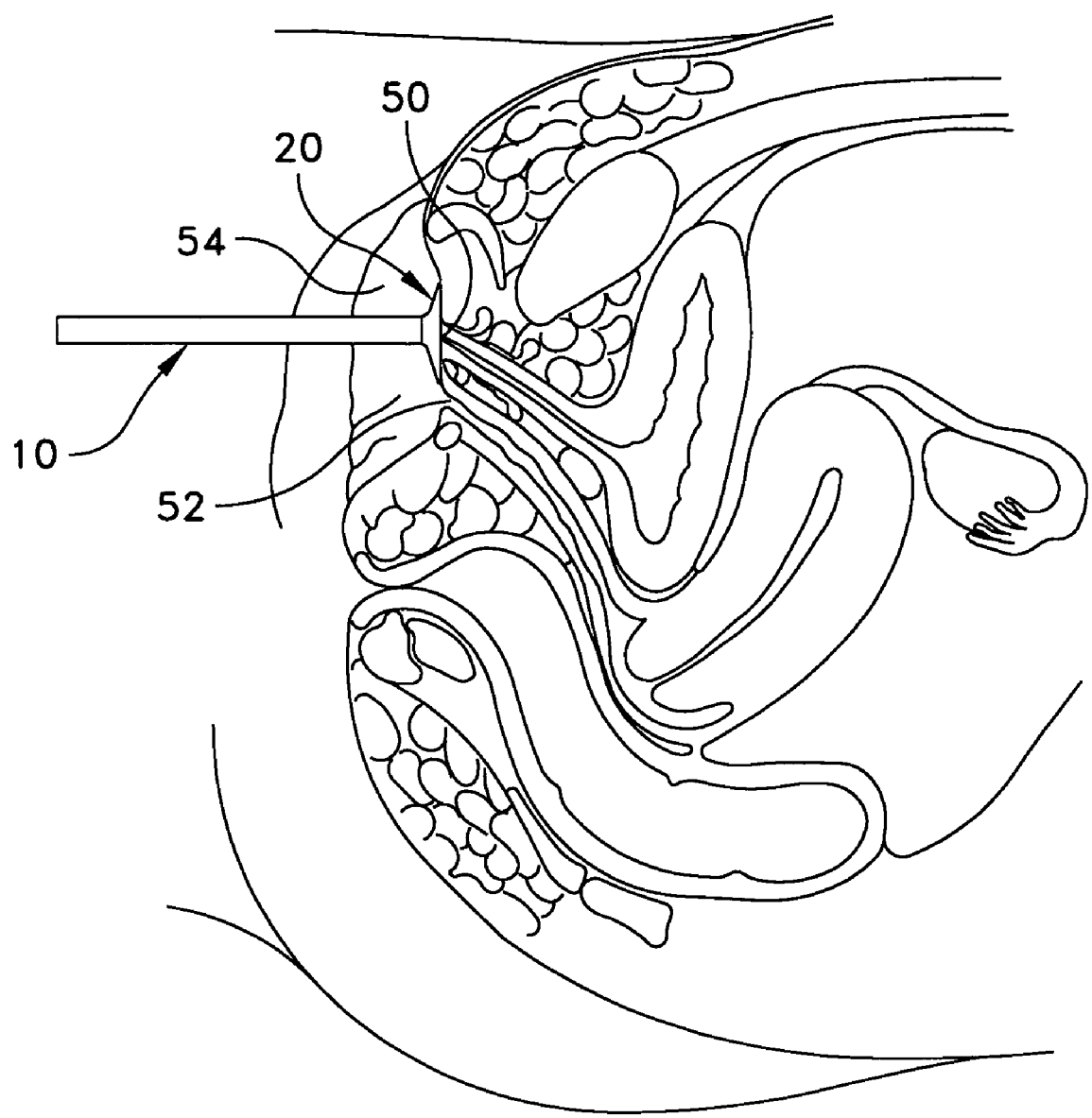
FIG. 10 is a cross-sectional view taken along line 10-10 of FIG. 9.

Reference is now made to a frontal view of the female anatomy showing such elements as the uretheral meatus at 50, the vagina at 52, labium minus at 54 and fossa navicularis at 56. FIGS. 7 and 8 also illustrate in perspective views anatomic members, particularly the uretheral meatus at 50, labium minus at 54 and fossa navicularis at 56. FIGS. 8-10 show the catheter of the present invention as applied over the uretheral meatus and between the side margins of the labium minus. FIG. 11 shows the catheter of the present invention as attached to a storage bag 60. The storage or collection bag 60 is illustrated as attached about the patient's leg by means of the straps 62. In use, the catheter has its pull-tab released so that the adhesive layer is exposed. Before the catheter is applied, the area around the urethera and fossa navicularis is cleaned. This accomplished by spreading the sides of the labium minus, washing the area thoroughly and patting the area dry. While holding the labium minus open with two fingers the medical practitioner applies the catheter by manually pressing at the distal facing contact surface 26 so as to adhere the annular proximal facing contact surface 25 at the fossa navicularis by means of the adhesive component 30. The resilient and deformable flared flange member 20 at its peripheral edge 24 is constructed and arranged so as to be within the bounds defined by the labium minus when applied. As also noted in FIG. 9, the catheter does not overlie the vagina and does not cover the greater vestibular gland (Bartholin's). Thus, there is not cross contamination where urine could progress to the vagina.

The pressure is maintained by the practitioner preferably for a minimum of 2 or 3 seconds. This pressure secures the catheter to the surface of the fossa navicularis such as illustrated in FIGS. 10 and 11. The end of the urinary tube 10 can then be attached to a drainage tube and collection bag, as shown in FIG. 11. The catheter can be attached for use with either a bedside drainage bag or a personal drainage bag. The bag preferably includes an absorbent pad that can be readily disposed of and replaced. The pad can be enclosed in a waterproof bag or pouch and attached to the catheter opening thus giving the wearer freedom of movement and obscurity from having such a device.

The wearer is free to wear normal street clothing such as a skirt, dress or pantsuit. The resilient and deformable flared flange member 20, in its applied position, establishes an alignment between the port 22 and the uretheral meatus 50. The catheter can be worn for extended periods of time without any adverse effects from urine drainage leaking into the vaginal cavity. The catheter can be worn for relatively long periods of time without any build-up of urine residue onto the patient because of its unique design characterized by a positive flow thus preventing any urinal track or vaginal infection from stagnant urine around the vaginal opening of the patient. Moreover, the catheter of the present invention is also one that can be easily applied by the user themselves.

After a period of time it is desired to replace the female catheter. It is preferred that replacement occurs about every two weeks. To do this the adhered flange member is simply gently peeled in a downward fashion from the prepuce of the clitoris, without causing any trauma to the area. A new catheter is then applied in the manner previously discussed.

The catheter of the present invention had associated therewith a number of important features relating particularly to the dimensional considerations of the catheter so that the catheter is effectively and readily applied. The urinary tube may have a length on the order of 3-6 inches. The resilient and deformable flange member is considered as having a somewhat funneled shape or more particularly a calla lily configuration with the flared part being quite pliable. In a frontal direction the resilient and deformable flange member is oval shaped at its peripheral edge 24.

In accordance with the present invention it has been found that there is a preferred range for the mean diameter of the flange member. With respect to, for example, the oval shape shown in FIG. 3, the mean diameter would be the average of the width and length dimensions. It has to be sufficiently large so as to provide an effective adhesive contact surface, and yet has to be sufficiently small so as to fit within the folds of the labium minus, as these folds actually assist in maintaining the catheter in place, at least at the initial stage of application. It has been found that the mean diameter of the peripheral edge is in a range between 15 and 30 millimeters. The thickness of the resilient and deformable flange member may be on the order of 1 millimeter or slightly greater than that. The wall thickness of the urinary tube may be greater than the thickness of the resilient and deformable flange member. The urinary tube wall thickness may be on the order of 1-2 millimeters. The thickness of the resilient and deformable flange member may be on the order of one millimeter. The area covered by the annular surface may be in a range on the order of 150-300 square millimeters. The inner diameter of the urinary tube part is preferably about 3 millimeter. The outer diameter of the urinary tube may be on the order of 6 millimeter.

In accordance with the method of the present invention this is for applying a female catheter at the uretheral meatus of the female anatomy for the purpose of enabling a discharge of urine through a urinary tube having proximal and distal ends intercoupling a passage for receiving therethrough the discharge of urine from the urethera. The urinary tube distal end is for coupling to a collection means. The method includes providing a resilient and deformable flared flange member that is formed integral with the proximal end of the urinary tube, that has a centered port contiguous with the urinary tube passage, that has a peripheral edge that at least in part defines an annular proximal facing contact surface and an opposed annular distal facing contact surface. An adhesive component is disposed on the annular proximal facing contact surface. The resilient and deformable flared flange member is applied by manual contact of the wearer with the annular distal facing contact surface so as to adhere the annular proximal facing contact surface at the fossa navicularis by means of the adhesive component. The applying step includes arranging the resilient and deformable flared flange member peripheral edge so as to be within the bounds defined by the labium minus when applied. The applying step further aligns the resilient and deformable flared flange member port with the uretheral meatus.

While preferred embodiments of the invention have now been described, it is understood by those skilled in the art that variations and modifications thereof can be made without departing from the spirit and scope of the present invention.

What is claimed is:

1. A female external catheter device comprising:
a urinary tube having proximal and distal ends intercoupling a passage for receiving therethrough the discharge of urine from the urethera a collection means;
said urinary tube distal end for coupling to a collection means;
said collection means comprising a storage bag, strap means for attaching the storage bag about the female leg and means for coupling the distal end of the urinary tube to the storage bag with the storage bag being positioned about the female leg so as to discharge urine under gravity from the urinary tube to the storage bag;
a single piece resilient and deformable flared flange member that is formed integral with the proximal end of the urinary tube, that has a centered port contiguous with the urinary tube passage, that has a closed and continuous peripheral edge that at least in part defines an annular proximal facing contact surface and an opposed annular distal facing contact surface, and that the closed and continuous peripheral edge covers an area that is greater than the cross-sectional area of the urinary tube;
the urinary tube being the only discharge passage for urine from the resilient and deformable flared flange member;
and an adhesive component disposed on the annular proximal facing contact surface and including a peel-off tab covering the adhesive component and removable to expose an adhesive layer;
said resilient and deformable flared flange member being applied by manual contact with the annular distal facing contact surface so as to adhere the adhesive layer on the annular proximal facing contact surface at the fossa navicularis by means of the adhesive component;
said resilient and deformable flared flange member closed and continuous peripheral edge constructed and arranged so as to be within the bounds defined by the labium minus when applied;
said resilient and deformable flared flange member in its applied position establishing an alignment between the port and the uretheral meatus;
wherein the resilient and deformable flange member is substantially oval shaped at its peripheral edge;
wherein the length L of the substantially oval shape is greater than the width W thereof, and with the width W extending to fit directly between the labium minus folds;
wherein the width W measured upwardly from the center of the centered port by a predetermined distance is less than the width W measured downwardly from the center of the centered port by the same predetermined distance so as to provide an asymmetric shape in an upward downward direction;
wherein the thickness of the resilient and deformable flange member is on the order of 1 millimeter and the closed and continuous peripheral edge of the resilient and deformable flared flange member terminates short of the vagina so as to expose the vagina;
wherein there is an absence of any catheter extending into the uretheral meatus as the urinary tube is the only means for discharge of urine from the uretheral meatus;
wherein the mean diameter of the closed and continuous peripheral edge is in a range between 15 and 30 millimeters;
wherein the closed and continuous peripheral edge of the single piece is resilient and deformable flared flange member is defined by a smooth, uninterrupted peripheral edge line;
wherein the wall thickness of the urinary tube is greater than the thickness of the resilient and deformable flange member;
and wherein the urinary tube wall thickness is on the order of 1-2 millimeters.

2. The female external catheter of claim 1 wherein the urinary tube has a length on the order of 3-6 inches.

3. The female external catheter of claim 1 wherein the outer diameter of the urinary tube is on the order of 6 millimeter.

4. The female external catheter of claim 1 wherein said resilient and deformable flange member is formed in a calla lily configuration.

5. The female external catheter of claim 1 wherein the area of the annular proximal facing contact surface is in a range on the order of 150-300 square millimeters.

* * * * *